US00PP36279P2

(12) United States Plant Patent
Heuger

(10) Patent No.: US PP36,279 P2
(45) Date of Patent: Nov. 26, 2024

(54) ***HELLEBORUS* PLANT NAMED 'HF 1116'**

(50) Latin Name: ***Helleborus* x *nigercors* X *Helleborus* x *hybridus***
Varietal Denomination: HF 1116

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 16 days.

(21) Appl. No.: 18/389,588

(22) Filed: Nov. 14, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'HF 1116, characterized by its upright to somewhat outwardly spreading and mounded plant habit; moderately vigorous to vigorous growth habit; dark green-colored leaflets with lighter green-colored venation; freely flowering habit; yellowish green-colored flowers; and good garden performance.

1 Drawing Sheet

Figure 2:
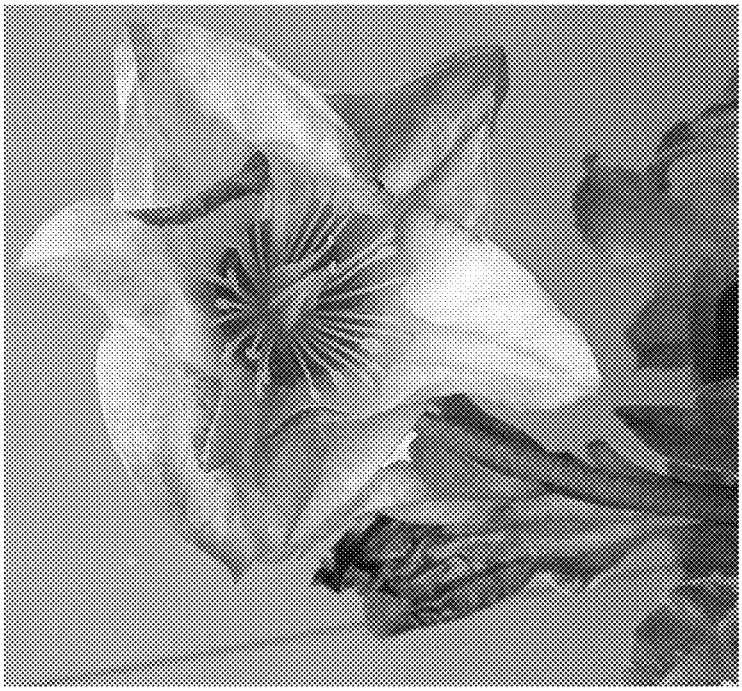

Botanical designation: *Helleborus* x *nigercors* X *Helleborus* x *hybridus.*

Cultivar denomination: 'HF 1116'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Nov. 30, 2022, application number 2022/2725. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *nigercors* X *Helleborus* x *hybridus* and hereinafter referred to by the name 'HF 1116'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in December, 2014 of a proprietary selection of *Helleborus* x *nigercors* identified as code number P544, not patented, as the female, or seed, parent and a proprietary selection of *Helleborus* x *hybridus* identified as code number O1426, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2016.

Asexual reproduction of the new *Helleborus* plant by in vitro axillary meristem culture in a controlled environment in Glandorf, Germany since April, 2017 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HF 1116'. These characteristics in combination distinguish 'HF 1116' as a new and distinct *Helleborus* plant:

1. Upright to somewhat outwardly spreading and mounded plant habit.
2. Moderately vigorous to vigorous growth habit.
3. Dark green-colored leaflets with lighter green-colored venation.
4. Freely flowering habit.
5. Yellowish green-colored flowers with purplish red-colored apical margins
6. Good garden performance.

Plants of the new *Helleborus* differ from plants of the female parent selection in the following characteristics:

1. Plants of the new *Helleborus* are more compact than plants of the female parent selection.

2. Flowers of plants of the new *Helleborus* are darker yellowish green in color than flowers of plants of the female parent selection.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are lighter yellowish green in color than flowers of plants of the male parent selection.

Plants of the new *Helleborus* can also be compared to plants of *Helleborus* x *ericsmithii* X *Helleborus* x *hybridus* 'COSEH 4200', disclosed in U.S. Plant Pat. No. 28,297. In side-by-side comparisons, plants of the new *Helleborus* differ primarily from plants of 'COSEH 4200' in the following characteristics:

1. Plants of the new *Helleborus* have smaller leaves than plants of 'COSEH 4200'.
2. Plants of the new *Helleborus* have smaller flowers than plants of 'COSEH 4200'.
3. Flowers of plants of the new *Helleborus* are yellowish green in color whereas flowers of plants of 'COSEH 4200' are pink in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

Figure 1:
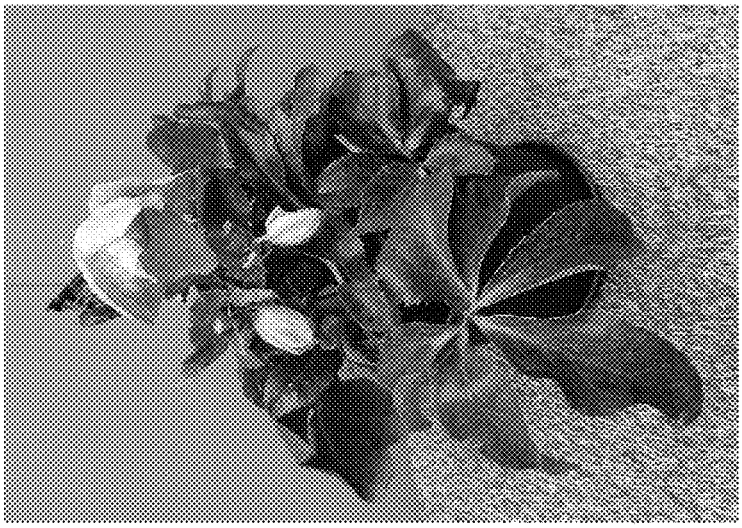

The photograph at the left of the sheet (FIG. 1) is a side perspective view of a typical flowering plant of 'HF 1116' grown in a container.

The photograph at the right of the sheet (FIG. 2) is a close-up view of a typical flower of 'HF 1116'.

DETAILED BOTANICAL DESCRIPTION

The aforementioned photographs and following observations, measurements and values describe plants grown during the early spring in 17-cm containers in a glass-covered greenhouse in Glandorf, Germany and under cultural practices typical of commercial *Helleborus* production. During the production of the plants, day temperatures ranged from 12C to 25C and night temperatures ranged from 5C to 12C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus* x *nigercors* X *Helleborus* x *hybridus* 'HF 1116'.

Parentage:

*Female, or seed, parent.*—Proprietary selection of *Helleborus* x *nigercors* identified as code number P544, not patented.

*Male, or pollen, parent.*—Proprietary selection of *Helleborus* x *hybridus* identified as code number O1426, not patented.

Propagation:

*Type.*—In vitro axillary meristem culture.

*Time to initiate roots, winter.*—About 55 days at temperatures about 12C.

*Time to produce a rooted young plant, winter.*—About 170 days at temperatures ranging from about 4C to 15C.

*Root description.*—Thick to thin, fleshy; typically white to brownish in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright to somewhat outwardly spreading and mounding plant habit with flowers held above the foliar plane; plant shape, inverted triangular; moderately vigorous to vigorous growth habit and moderate growth rate.

*Plant height, soil level to top of foliar plane.*—About 22.7 cm.

*Plant height, soil level to top of flowers.*—About 42 cm.

*Plant diameter* (*area of spread*).—About 56.5 cm.

Leaf description:

*Arrangement.*—Leaves arranged in a basal rosette; leaves palmately compound with typically five leaflets per leaf.

*Leaf length.*—About 15.2 cm.

*Leaf width.*—About 18.2 cm.

*Leaflet length.*—About 10.7 cm.

*Leaflet width.*—About 6 cm.

*Leaf shape.*—Palmate; roughly reniform in outline.

*Leaflet shape.*—Broadly elliptic to ovate or obovate.

*Leaflet apex.*—Acute.

*Leaflet base.*—Broadly attenuate.

*Leaflet margin.*—Serrate; coarsely undulate.

*Leaflet texture and luster, upper surface.*—Smooth, glabrous; coriaceous and tough; slightly to moderately glossy.

*Leaflet texture and luster, lower surface.*—Smooth, glabrous; coriaceous and tough; slightly glossy.

*Leaflet venation pattern.*—Pinnate and reticulate.

*Leaflet color.*—Developing leaflets, upper surface: Close to NN137B; midvein, proximally, tinged with close to 187C. Developing leaflets, lower surface: Close to 146A; venation, close to 184A. Fully developed leaflets, upper surface: Darker than a blend of NN137A and 147A; venation, close to 144A; midvein, proximally, tinged with close to 200C. Fully developed leaflets, lower surface: Close to 147B; venation, close to 146D.

*Petioles.*—Length: About 13.9 cm. Diameter: About 5.5 mm by 6 mm. Strength: Strong. Texture and luster, upper and lower surfaces: Smooth, glabrous; moderately glossy. Color, upper surface: Close to 146B; sparsely covered with fine dots and stripes, close to 165A. Color, lower surface: Close to 146B; moderately to heavily covered with fine dots and stripes, close to 165A.

Flower description:

*Flower shape and habit.*—Single rotate bowl-shaped flowers arranged in panicles; freely flowering habit with about six to eleven flowers per inflorescence and about 60 flowers and flower buds per plant; flowers face mostly outwardly to slightly nodding.

*Fragrance.*—None detected.

*Natural flowering season.*—Plants begin flowering about ten months after planting; plants flower naturally from late winter into the spring in Germany.

*Flower longevity on the plant.*—About ten days; sepals persistent, other flower parts are not persistent.

*Flower buds.*—Length: About 2.6 cm. Diameter: About 1.6 cm. Shape: Ovate. Texture and luster: Smooth, glabrous; matte. Color: Close to 145B; margins, close to 185B.

*Inflorescence height (including peduncle).*—About 35.8 cm.

*Inflorescence diameter.*—About 23.2 cm.

*Flower diameter.*—About 6.7 cm.

*Flower depth.*—About 2.8 cm.

*Petals.*—All petals are transformed into nectaries.

*Sepals.*—Quantity and arrangement: About five, arranged in a single whorl. Length: About 3.9 cm. Width: About 3.7 cm. Shape: Broadly ovate; slightly concave. Apex: Broadly and bluntly acute. Base: Rounded to broadly cuneate. Margin: Entire; slightly undulate. Texture and luster, upper surface: Smooth, glabrous; matte. Texture and luster, lower surface: Smooth, glabrous; matte to slightly glossy. Color: When opening, upper surface: Close to 145B; towards the margins and apex, close to 186A; at the base, close to 144C. When opening, lower surface: Close to 145C; towards the margins and apex, close to a blend of 185B and 186A; venation, close to 185B. Fully opened, upper surface: Close to 145B to 145D; towards the margins and apex, close to 186A; at the base, close to 144C; venation, similar to lamina colors; color does not change with subsequent development. Fully opened, lower surface: Close to 145C to 145D; towards the margins and apex, close to 187D; venation, close to 187D; color does not change with subsequent development.

*Flower bracts.*—Quantity per flower: Typically one. Length: About 5.9 cm. Width: About 3.5 cm. Shape: Ovate to obovate. Apex: Acute to three-lobed with acute apices. Base: Truncate to cuneate. Margin: Proximally, entire; distally, finely serrate; slightly coarsely undulate. Color, upper surface: Close to NN137A; towards the base, close to 144A. Color, lower surface: Close to a blend of 146B and 147B; midvein, close to 166A to 166B.

*Peduncles.*—Length: About 24.5 cm. Diameter: About 7 mm to 9 mm. Aspect: About 20 degrees from vertical. Strength: Strong. Texture and luster: Smooth, glabrous; moderately glossy. Color: Close to 146B; heavily covered with fine dots, close to 183A to 183B.

*Pedicels.*—Length: About 2.1 cm. Diameter: About 3 mm. Aspect: About 25 degrees from peduncle axis. Strength: Moderately strong. Texture and luster: Smooth, glabrous; moderately glossy. Color: Close to 152B to 152C.

*Reproductive organs.*—Stamens: Quantity per flower: About 70. Filament length: About 1.6 cm. Filament color: Close to 157D. Anther shape: Double and broadly reniform; basifixed. Anther size: About 1.75 mm by 2.5 mm. Anther color: Close to 150C. Pollen amount: Sparse. Pollen color: Close to 4D to lighter than 4D. Pistils: Quantity per flower: About four to five. Pistil length: About 1.3 cm. Stigma diameter: About 0.3 mm. Stigma shape: Club-shaped. Stigma color: Close to 154C. Style length: About 1.25 mm. Style color: Close to 182B; proximally, close to 182D. Ovary color: Close to 144B. Nectaries (transformed petals): Quantity per flower: About 11 to 15. Length: About 1.2 cm. Diameter: About 6 mm. Shape: Tubular, flattened; apices, obtuse. Texture and luster, inner and outer surfaces: Smooth, glabrous; slightly glossy. Color, immature, inner and outer surfaces: Close to 144B; towards the apex, close to N144A. Color, mature, inner surface: Close to 144C; towards the apex, close to 151B; venation, similar to lamina colors; with subsequent development, color becoming closer to N144A and towards the apex, closer to 153B. Color, mature, outer surface: Close to 144C; towards the apex, close to 151B; at the base, close to 144A to 144B; venation, similar to lamina colors; with subsequent development, color becoming closer to N144A, towards the apex, closer to 153B and at the base, close to 152D. Seeds and fruits: To date, seed and fruit development have not been observed on plants of the new *Helleborus.*

Garden performance: Plants of the new *Helleborus* have been observed to have good garden performance and to tolerate rain, wind, high temperatures about 35C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HF 1116' as illustrated and described.

* * * * *